(12) United States Patent
Reiderman

(10) Patent No.: US 8,037,765 B2
(45) Date of Patent: Oct. 18, 2011

(54) ELECTROMAGNETIC ACOUSTIC TRANSDUCER USING MAGNETIC SHIELDING

(75) Inventor: Arcady Reiderman, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 406 days.

(21) Appl. No.: 11/933,970

(22) Filed: Nov. 1, 2007

(65) Prior Publication Data
US 2009/0114022 A1 May 7, 2009

(51) Int. Cl.
*G01N 29/24* (2006.01)
(52) U.S. Cl. .................................................. 73/643
(58) Field of Classification Search .................. 73/643; 367/35, 140
See application file for complete search history.

(56) References Cited

U.S. PATENT DOCUMENTS

| | | | |
|---|---|---|---|
| 4,232,557 A * | 11/1980 | Vasile | 73/629 |
| 4,296,486 A | 10/1981 | Vasile | 367/140 |
| 4,716,556 A | 12/1987 | Raskin et al. | |
| 5,050,703 A * | 9/1991 | Graff et al. | 181/106 |
| 5,148,414 A * | 9/1992 | Graff et al. | 367/140 |
| 5,164,921 A * | 11/1992 | Graff et al. | 367/140 |
| 5,436,873 A * | 7/1995 | MacLauchlan et al. | 367/140 |
| 6,176,132 B1 * | 1/2001 | MacLauchlan | 73/290 V |
| 6,452,388 B1 | 9/2002 | Reiderman et al. | 324/303 |
| 6,839,640 B2 | 1/2005 | Ohtani | |
| 6,951,133 B2 | 10/2005 | Passarelli, Jr. | |
| 7,024,935 B2 | 4/2006 | Paige et al. | 73/643 |
| 7,426,867 B2 * | 9/2008 | Koch et al. | 73/627 |
| 2005/0205248 A1 | 9/2005 | Barolak et al. | |
| 2007/0211572 A1 * | 9/2007 | Reiderman et al. | 367/35 |
| 2007/0216416 A1 | 9/2007 | Itskovich | |

* cited by examiner

*Primary Examiner* — John Chapman, Jr.
(74) *Attorney, Agent, or Firm* — Mossman Kumar & Tyler PC

(57) ABSTRACT

A combined electromagnetic acoustic transducer (EMAT) is disclosed that uses magnetic shielding to increase the efficiency (defined as the received signal per unit of excitation current). In addition, electromagnetic shielding may also be used to reduce the direct coupling between the transmit and receive coils.

19 Claims, 24 Drawing Sheets

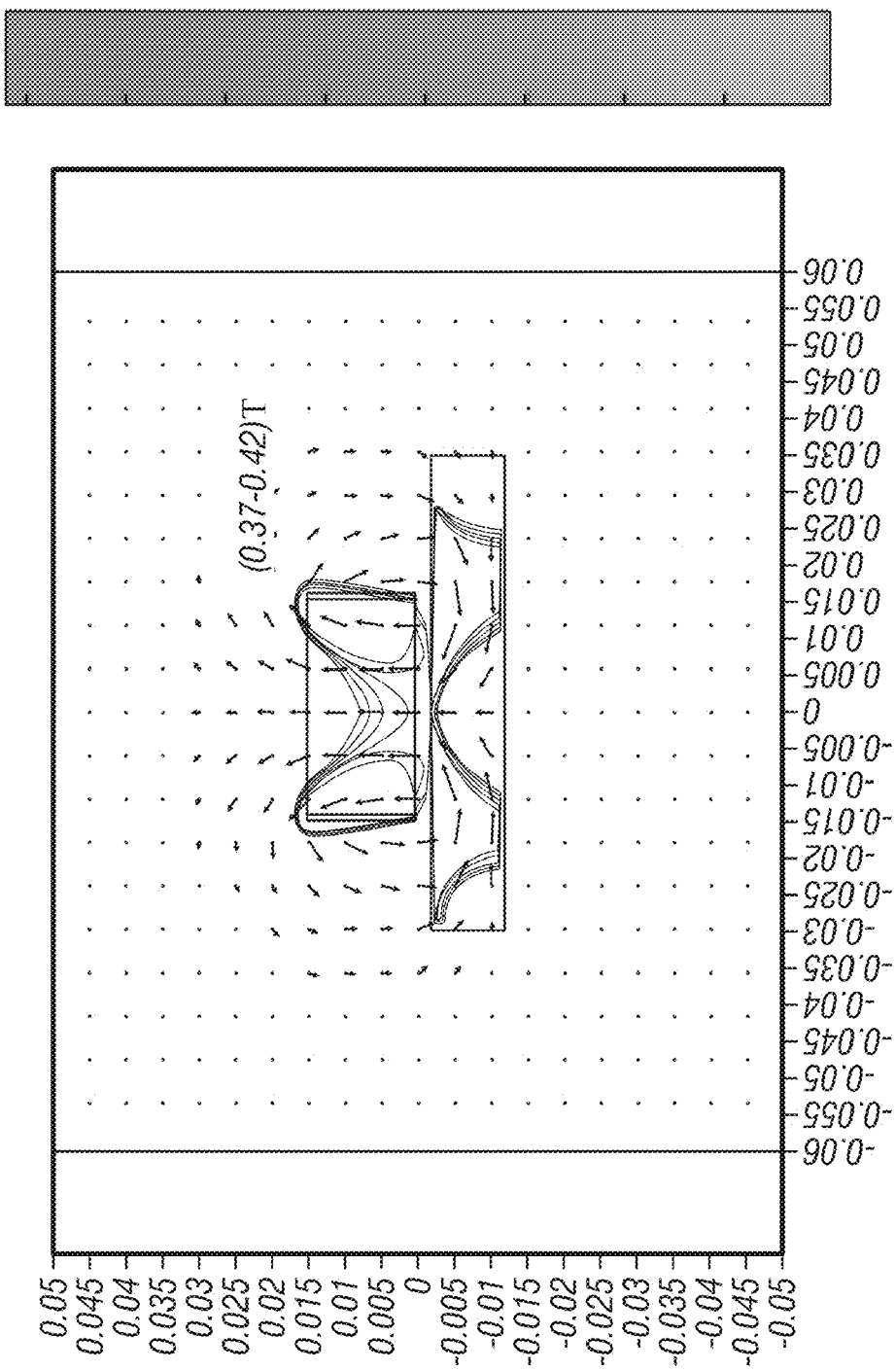

ELECTROMAGNETIC ACOUSTIC TRANSDUCER USING MAGNETIC SHIELDING

BACKGROUND OF THE DISCLOSURE

1. Field of the Disclosure

The disclosure relates generally to the field evaluating the integrity of bonds that adhere wellbore casing to a wellbore. More specifically, the present disclosure relates to a method and apparatus of producing and detecting acoustic forces within a wellbore casing to evaluate the integrity of the casing.

2. Description of Related Art

As illustrated in FIG. 1 wellbores typically comprise casing 8 set within the wellbore 5, where the casing 8 is bonded to the wellbore by adding cement 9 within the annulus formed between the outer diameter of the casing 8 and the inner diameter of the wellbore 5. The cement bond not only adheres to the casing 8 within the wellbore 5, but also serves to isolate adjacent zones (e.g. $Z_1$ and $Z_2$) within an earth formation 18. Isolating adjacent zones can be important when one of the zones contains oil or gas and the other zone includes a non-hydrocarbon fluid such as water. Should the cement 9 surrounding the casing 8 be defective and fail to provide isolation of the adjacent zones, water or other undesirable fluid can migrate into the hydrocarbon producing zone thus diluting or contaminating the hydrocarbons within the producing zone, and increasing production costs, delaying production or inhibiting resource recovery.

To detect possible defective cement bonds, downhole tools 14 have been developed for analyzing the integrity of the cement 9 bonding the casing 8 to the wellbore 5. These downhole tools 14 are lowered into the wellbore 5 by wireline 10 in combination with a pulley 12 and typically include transducers 16 disposed on their outer surface formed to be acoustically coupled to the fluid in the borehole. These transducers 16 are generally capable of emitting acoustic waves into the casing 8 and recording the amplitude of the acoustic waves as they travel, or propagate, across the casing 8. Characteristics of the cement bond, such as its efficacy, integrity and adherence to the casing, can be determined by analyzing characteristics of the acoustic wave such as attenuation. Typically the transducers 16 are piezoelectric devices having a piezoelectric crystal that converts electrical energy into mechanical vibrations or oscillations transmitting acoustic wave to the casing 8. Piezoelectric devices typically couple to a casing 8 through a coupling medium found in the wellbore. Coupling mediums include liquids that are typically found in wellbores. When coupling mediums are present between the piezoelectric device and the casing 8, they can communicate the mechanical vibrations from the piezoelectric device to the casing 8. However, lower density fluids such as gas or air and high viscosity fluids such as some drilling mud may not provide adequate coupling between a piezoelectric device and the casing 8. Furthermore, the presence of sludge, scale, or other like matter on the inner circumference of the casing 8 can detrimentally affect the efficacy of a bond log acquired with a piezoelectric device. Thus for piezoelectric devices to provide meaningful bond log results, they must cleanly contact the inner surface of the casing 8 or be employed in wellbores, or wellbore zones, having liquid within the casing 8. Another drawback faced when employing piezoelectric devices for use in bond logging operations involves the limitation of variant waveforms produced by these devices. Fluids required to couple the wave from the transducer to the casing only conduct compressional waves, thus limiting the wave types that can be induced in or received from the casing. A great deal of information is derivable from variant acoustical waveforms that could be used in evaluating casing, casing bonds, and possibly even conditions in the formation 18. Therefore, there exists a need to conduct bond logging operations without the presence of a particular couplant. A need exists for a bond logging device capable of emitting and propagating into wellbore casing numerous types of waveforms, and recording the waveforms.

Electromagnetic-acoustic transducers (EMATs) have been used in non-destructive testing. An EMAT acts through the following physical principles. When a wire is placed near the surface of an electrically conducting object and is driven by a current at the desired ultrasonic frequency, eddy currents are induced in a near surface region of the object. If a static magnetic field is also present, these eddy currents experience Lorentz forces. These forces cause an acoustic excitation in the object. In a reciprocal use, an electric signal will be generated in the wire as a result of acoustic excitation in a metal placed close to a permanent magnet. Attenuation and/or reflection of the acoustic waves bear information on the defects and surroundings of the object. An EMAT is typically designed to producing a single waveform, such as shear horizontal waves (SH) or Lamb waves.

Various EMAT design configurations have been proposed. U.S. Pat. No. 4,296,486 to Vasile discloses an EMAT including a source of magnetic flux for establishing a static magnetic field, an electrical conductor for conducting an alternating current in the static magnetic field, and an electrically conductive nonmagnetic shield disposes between the source of magnetic flux and the conductor. U.S. Pat. No. 7,024,935 to Paige et al. discloses an EMAT including a magnetic unit arranged to be moved relative to the material under test to magnetize a surface layer of the material, and an electrical winding supplied by an alternating current source, the magnetic unit and the electric winding, in use, being applied in sequence to the material under test whereby the electrical winding is positioned adjacent the material subsequent to magnetization thereof by the magnetic unit, the alternating magnetic flux created by the winding interacting with the remnant magnetization of the material to create ultrasonic vibration of the material.

As for all downhole applications, it would be desirable to increase the transducer efficiency. In addition, as in most sensors using EM antennas, it would be desirable to reduce the effects of transmitter-receiver coupling and the effects of the object being examined on the antenna impedance. The present disclosure addresses this need.

SUMMARY OF THE DISCLOSURE

One embodiment of the disclosure is an apparatus for evaluating a tubular. The apparatus includes an electromagnetic coupling device having a coil, a magnet, and a magnetic shield configured to be conveyed into the tubular and couple acoustic energy within the tubular. The coupling device may be further configured to propagate an acoustic wave in the tubular. The coupling device may be further configured to record an acoustic wave propagating in the tubular. The magnetic shield may include an nonconductive soft magnetic material having a high saturation flux density and low radio frequency losses. The apparatus may further include an electromagnetic shield. The electromagnetic coupling device may be further configured to form a wave within the tubular, the wave having a polarization that is that of a compressional wave, a shear wave, a transversely polarized shear wave, a Lamb wave an/or a Rayleigh wave. The tubular may be a casing in a wellbore and apparatus may include a logging tool including the electromagnetic coupling device. The apparatus may include a plurality of the electromagnetic coupling devices on the logging tool. The plurality of electromagnetic coupling devices may be axially and/or circumferentially spaced apart. The apparatus may further include a processor configured to determine a velocity of propagation of an acoustic wave in the tubular using a signal generated by one of the plurality of electromagnetic coupling devices and received by another of the plurality of electromagnetic coupling devices.

Another embodiment is a method of evaluating a tubular. The method includes conveying an electromagnetic coupling device having a coil, a magnet, and a magnetic shield into the tubular, conveying an electrical current to the coil, and coupling acoustic energy to the tubular. Coupling the acoustic energy may further include propagating an acoustic wave in the tubular, or recording an acoustic wave propagating in the tubular. That method may further include using, as the magnetic shield, a soft magnetic material having a high saturation flux density and low RF losses. The method may further include using an electromagnetic shield. The method may further include using the electromagnetic coupling device to form a wave within the tubular, the wave having a polarization that is that of one of a compressional wave, a shear wave, a transversely polarized shear wave, a Lamb wave and/or a Rayleigh wave. The tubular may be a casing in the wellbore and method may further include disposing the electromagnetic coupling device on a logging tool. The method may further include using a plurality of electromagnetic coupling devices disposed on the logging tool. The method may further include positioning the plurality of electromagnetic coupling devices axially and/or circumferentially spaced apart. The method may further include determining a velocity of propagation of an acoustic wave in the tubular using a signal generated by one of the electromagnetic coupling devices and received by another of the plurality of electromagnetic coupling devices.

Another embodiment is a computer-readable medium for use with an apparatus for evaluating a tubular. The apparatus includes an electromagnetic coupling device comprising a coil, a magnet and a magnetic shield configured to be conveyed into the tubular and coupling acoustic energy within the tubular, and a source of electrical current configured to convey current to the coil. The medium includes instructions that enable at least one processor to use the electromagnetic coupling device to produce a wave in the tubular having a polarization that is that of a compressional wave, a shear wave, a transversely polarized shear wave, a Lamb wave, and/or a Rayleigh wave. The medium may include a ROM, an EPROM, an EEPROM, a flash memory, and/or an optical disk.

BRIEF DESCRIPTION OF THE DRAWINGS

The present disclosure and its advantages will be better understood by referring to the following detailed description and the attached drawings in which:

FIGS. 10(a), 10(b) and 10(c) show results of 2-D simulation of the transducer of FIG. 9 showing the isolines of the static magnetic field, the RF magnetic field, and the RF magnetic field with the assumption of a non-conductive magnet;

DETAILED DESCRIPTION OF THE DISCLOSURE

Figure 1:
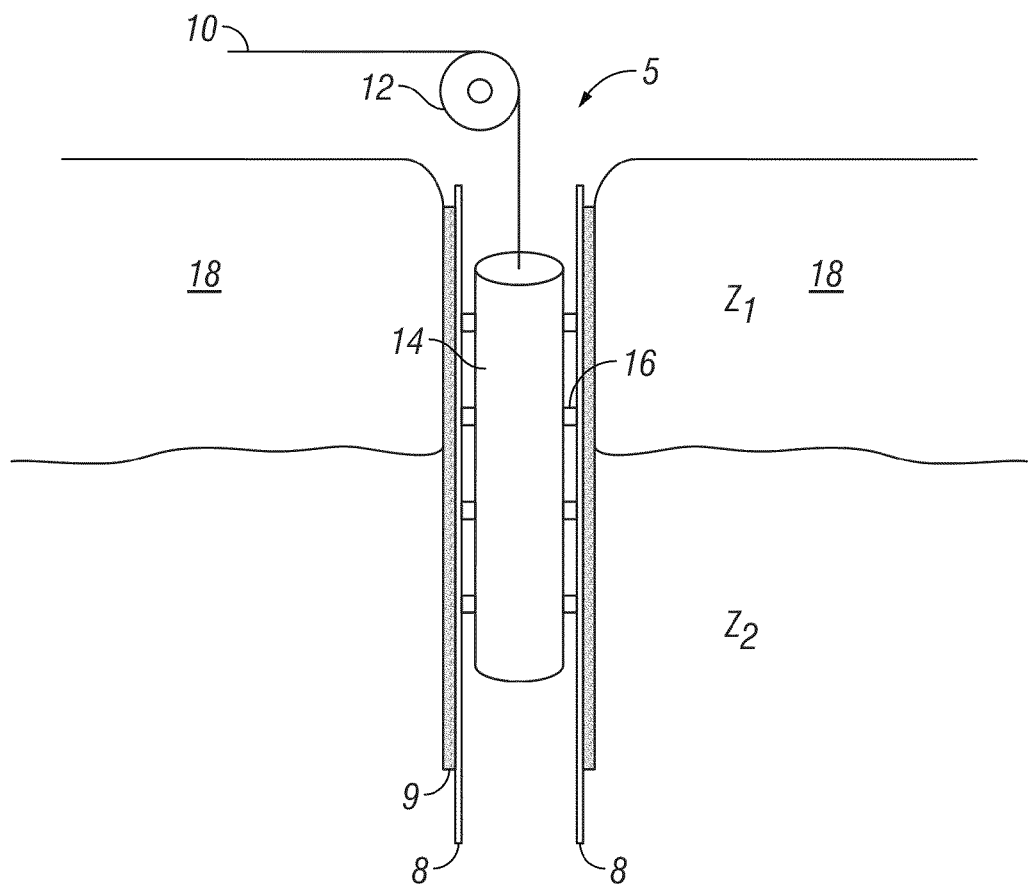
FIG. 1 depicts a partial cross section of prior art downhole cement bond log tool disposed within a wellbore.
Figure 2:
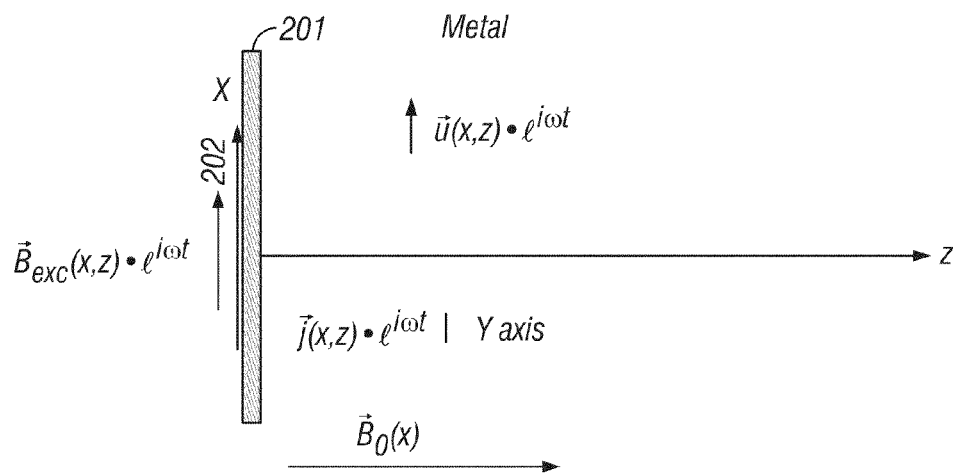
FIG. 2 shows the field configuration of an EMAT.

FIG. 2 shows basic geometry for the shear wave excitation based on Lorenz force. A current $i_{axc}(x,z)e^{i\omega t}$ indicated by 202 flows in the x-direction proximate to a metal body 201. This induces a current $j_{exc}(x,z)e^{i\omega t}$ in the y direction in the metal which then produces a displacement $u_{exc}(x,z)e^{i\omega t}$ in the metal. The three equations below represent respectively the acoustic amplitude, the receiver signal and the transducer efficiency defined as receive signal per unit current in the transmit wire:

$$u \propto \frac{B_0 \cdot B_{exc}}{d \cdot s}, \text{ for } \delta \ll \lambda_a, \quad (1)$$

$$S_r \propto u \cdot B_0 \cdot \frac{B_r}{I_r}, \quad (2)$$

$$\frac{S_r}{I_{RF}} \propto B_0^2 \cdot \left(\frac{B_r}{I_r}\right) \cdot \left(\frac{B_{exc}}{I_{exc}}\right). \quad (3)$$

Here, u is the acoustic amplitude, $B_0$ is the static magnetic field, $B_{exc}$ is the excitation magnetic field generating eddy currents in the object, d is the density, s is the shear modulus, $$\frac{B_r}{I_r}$$

the receiver sensitivity function (defined based on reciprocity principle as the magnetic field generated magnetic field per unit current), $$\frac{B_{exc}}{I_{exc}}$$

is the magnetic field per unit current for the excitation coil (if the same coil is used for transmit and receive modes of the transducer, then $$\frac{B_r}{I_r} = \frac{B_{exc}}{I_{exct}}\Bigg),$$

δ is the electromagnetic skin depth in the object for excitation frequency, and λ is the wavelength of the acoustic excitation. In what follows below, modeling results for different transducer configurations are compared using static magnetic field flux density and the RF magnetic field flux density per unit current as criteria.

Figure 3:
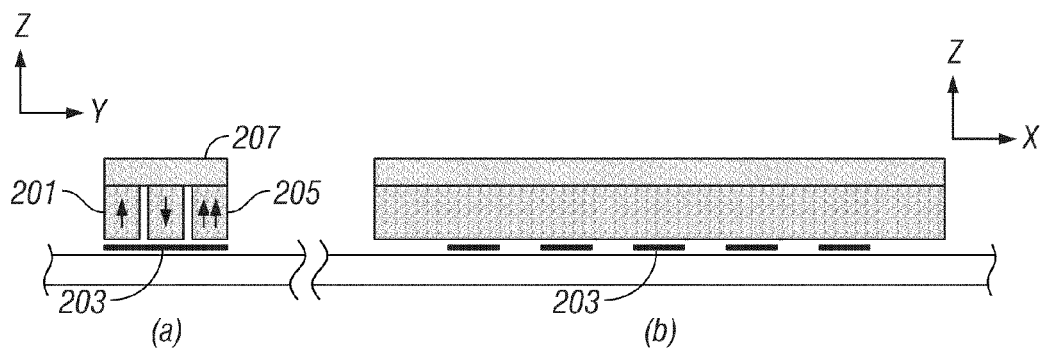
FIG. 3(a)-(b) (prior art) shows a layout of a prior art transducer for shear wave generation.

FIG. 3(a)-(b) shows layout of a transducer for the shear wave generation. The acoustic wavelength is defined by the spatial period of the static magnetic field generation (magnetization directions of the magnets are shown by arrows in FIG. 3). A desired excitation mode is selected by choosing the operation frequency at which the transmitter wire is driven by the excitation current. The object being examined is denoted by 201. The magnet is denoted by 207 with the directional arrows indicating the polarity of the magnets. The back iron is denoted by 205 and the transmit and receive wires by 203.

Figure 4A:
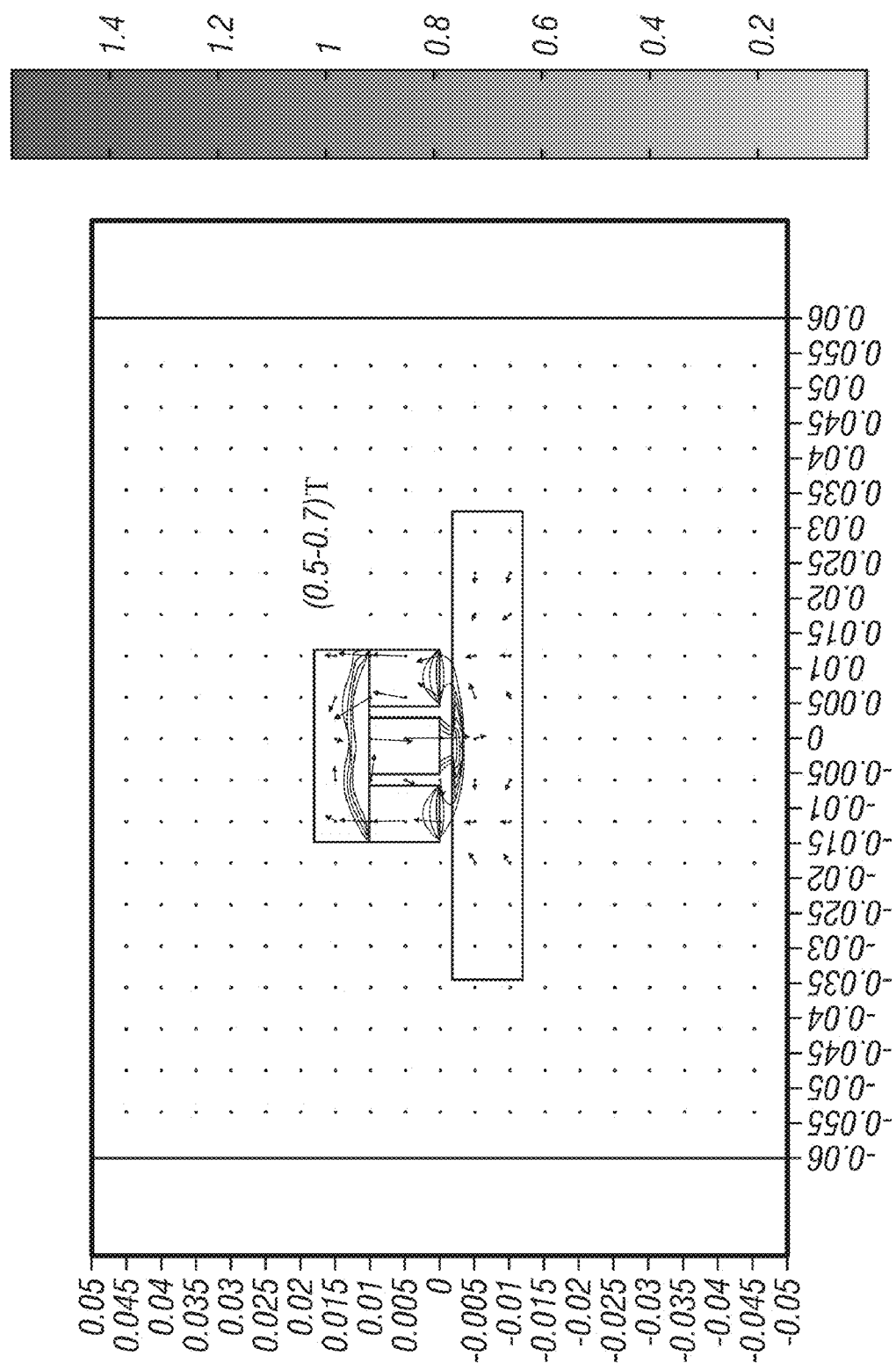
FIGS. 4(a), 4(b) and 4(c) show results of 2-D simulation of the transducer of FIG. 3 showing the isolines of the static magnetic field, the RF magnetic field, and the RF magnetic field with the assumption of a non-conductive magnet.
Figure 4B:
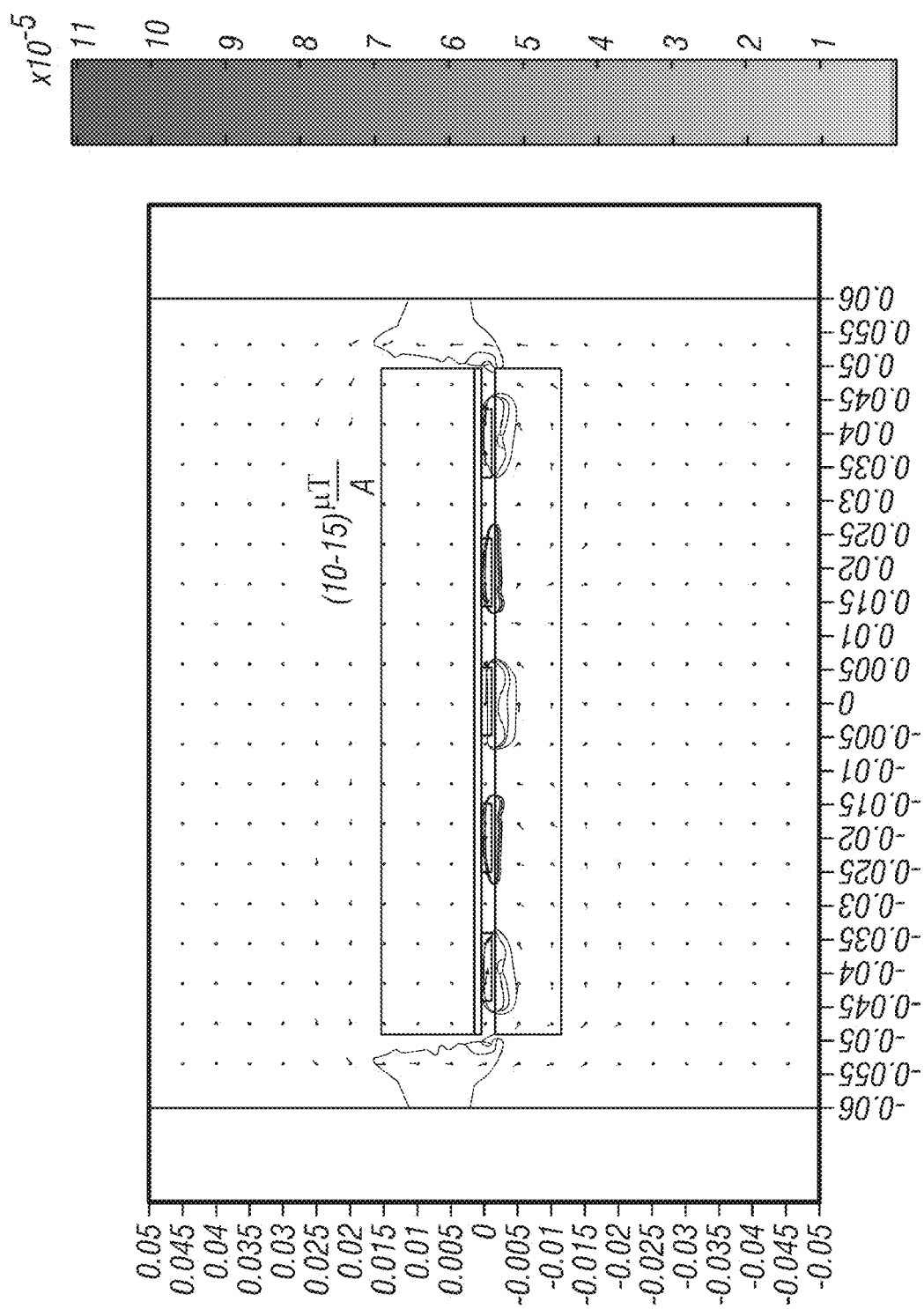
Figure 4C:
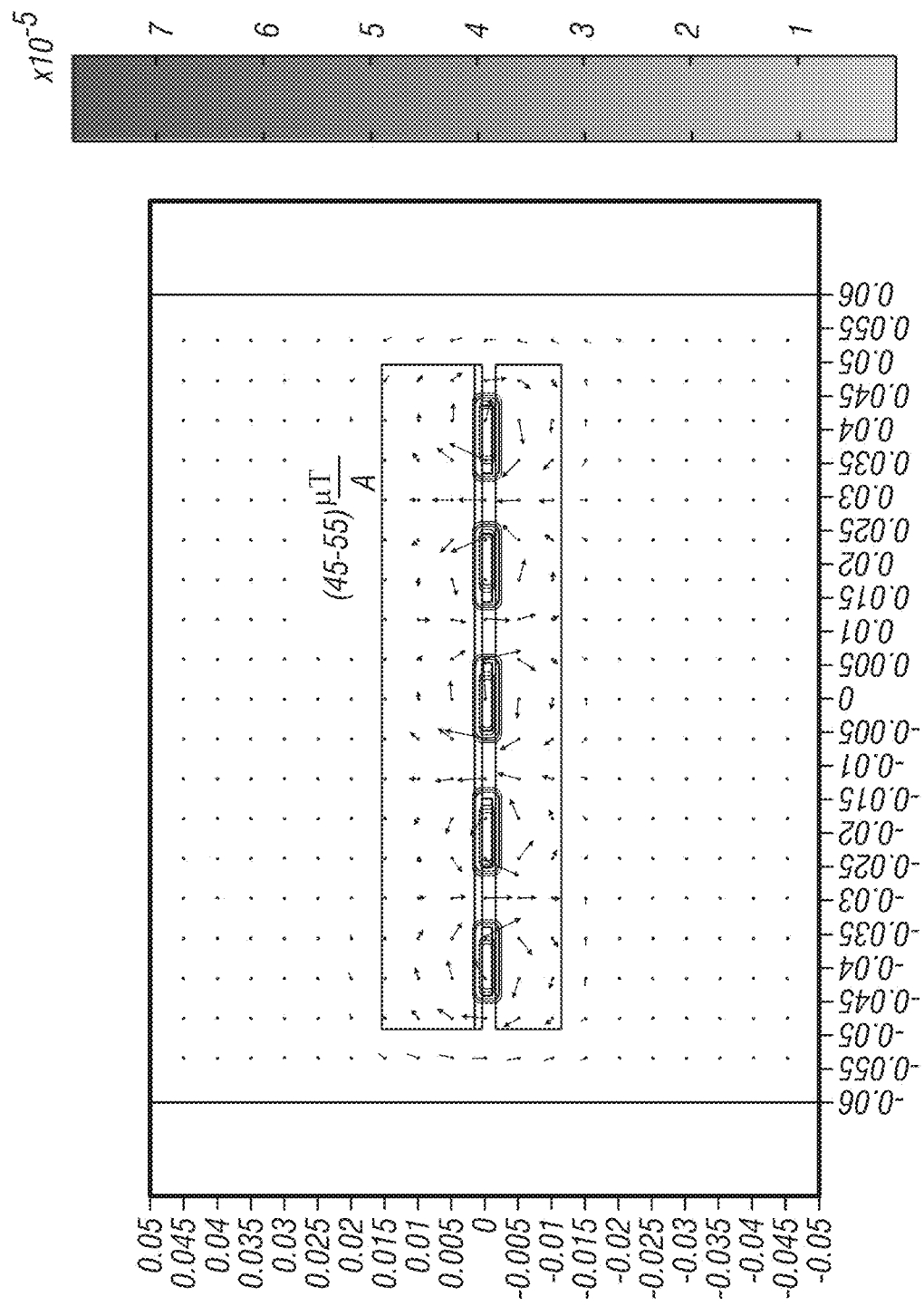

FIG. 4(a) shows the results of 2-D simulation for the configuration of FIG. 3. Shown therein are the iso-field lines representing the static magnetic field. FIG. 4(b) shows the results of 2-D simulation with the iso-field lines representing the RF magnetic field of the transducer. In order to show the primary RF field only, the object conductivity was set zero at the excitation surface. FIG. 4(c) shows the results of 2-D simulation with the iso-field lines representing the RF magnetic field of the transducer with the assumption that the magnet is nonconductive. FIGS. 4(a)-4(c) also give scale for the display. Comparing FIG. 4(b) with 4(c), we see that the presence of a conductive magnet in FIG. 4(b) reduces the RF magnetic field by a factor of about 4. Since non-conductive magnets are typically one-third the strength of conductive magnets, the use of a non-conductive magnet would cause almost 10 time reduction in $B_0^2$ term of the equation (3). Therefore, the following embodiments of the transducer are discussed.

Figure 5:
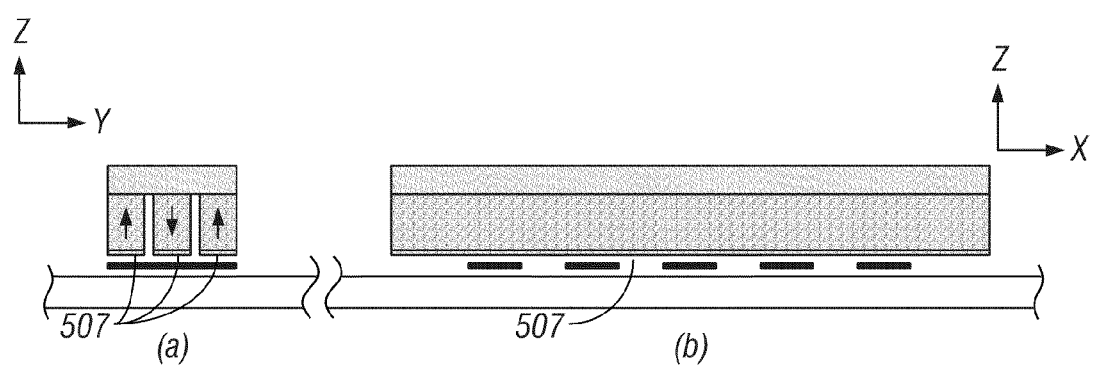
FIG. 5 shows the layout of a modified transducer.
Figure 6A:
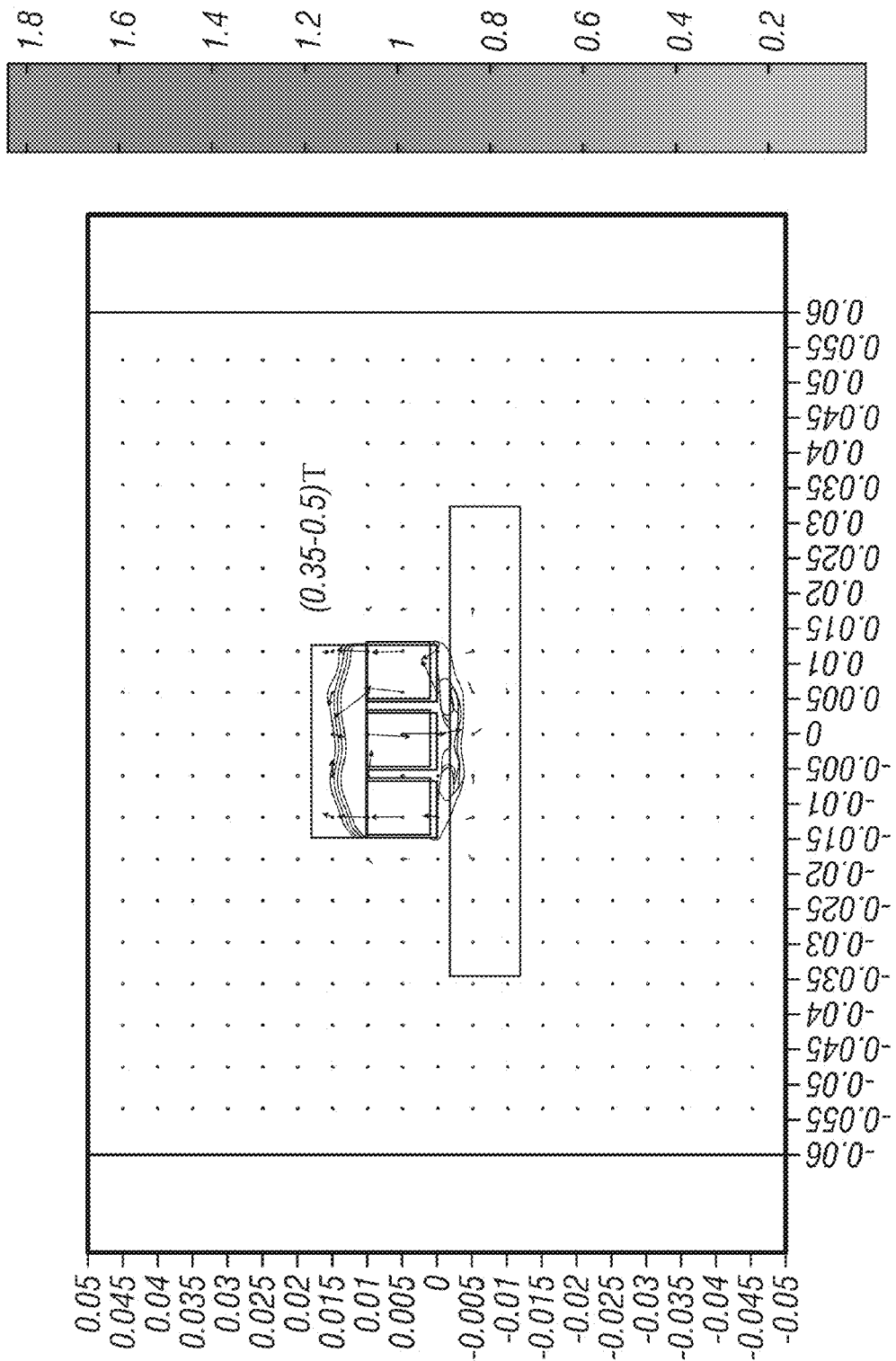
FIGS. 6(a) and 6(b) show results of 2-D simulation of the transducer of FIG. 5 showing the isolines of the static magnetic field and the RF magnetic field.
Figure 6B:
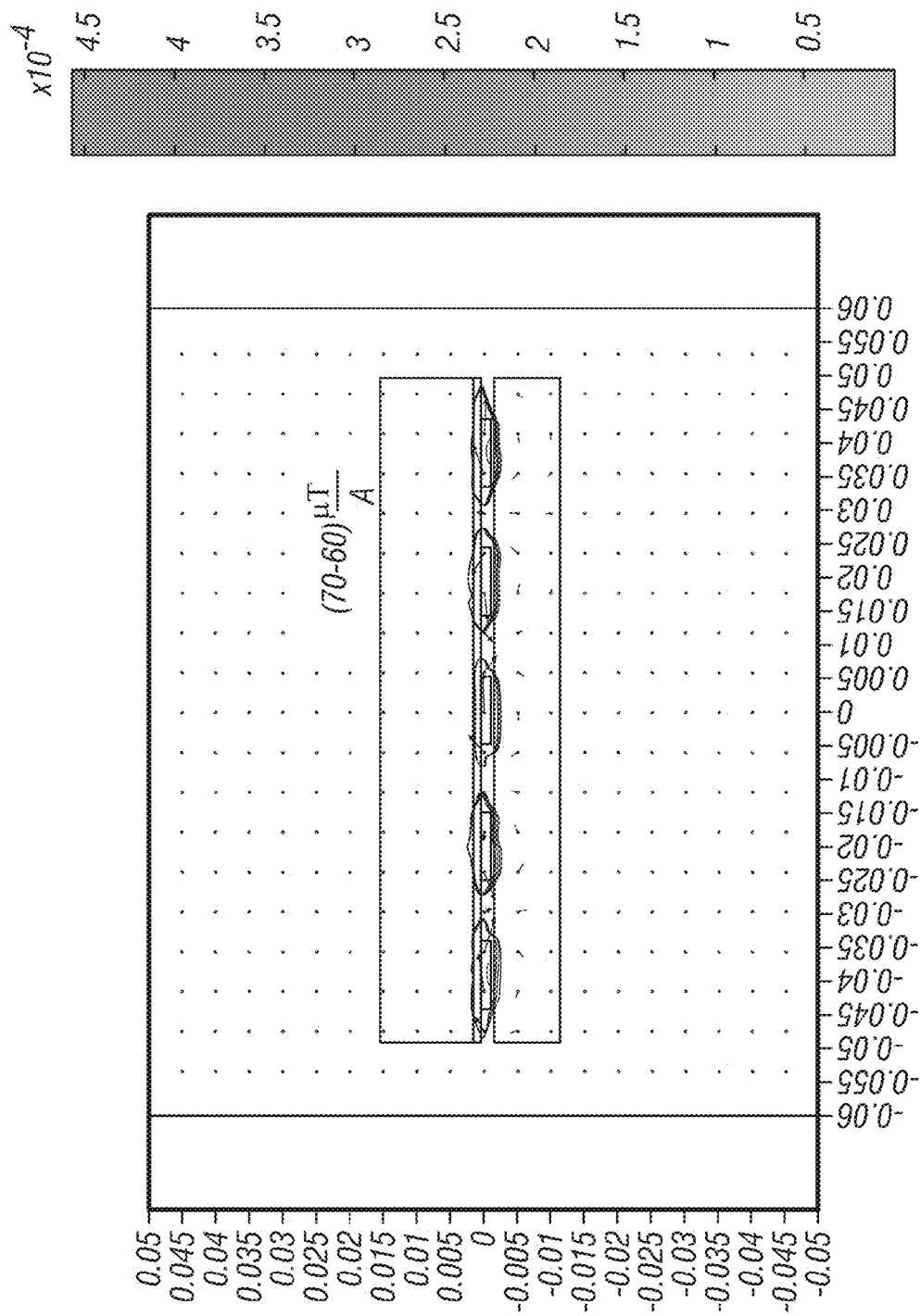

FIG. 5 shows layout of a modified transducer. The major difference with the transducer of FIG. 3 is the addition of soft magnetic shoes 507. The shoes act as a magnetic shield concentrate RF flux resulted in boosting the RF magnetic field at the object surface and shields the conductive magnet from the RF field of the wire. FIG. 6(a) shows the results of 2-D simulation for the configuration of FIG. 5. Shown therein are the iso-field lines representing the static magnetic field. FIG. 6(b) shows the results of 2-D simulation with the iso-field lines representing the RF magnetic field of the transducer. Again, in order to show the primary RF field only, the object conductivity was set zero at the excitation surface. The modeling results show a slight reduction in the static magnetic field and a dramatic increase in the RF field per unit current.

Compare $$\frac{(70-60)\mu T}{A}$$

in FIG. 6(b) with $$\frac{(10-15)\mu T}{A}$$

in FIG. 4(b).

It is important to note that the soft magnetic material to be used in this application should possess a high saturation flux density and low RF losses in the frequency range up to 1 MHz. In application to EMAT the soft magnetic material may not have high magnetic permeability since the effective permeability of the magnetic shoes is predominantly shape limited. From a practical standpoint, the permeability of the material could be as low as 10-20. Use of this type of materials as an antenna core in a NMR sensor is disclosed in the U.S. Pat. No. 6,452,388 to Reiderman et al.

Figure 7:
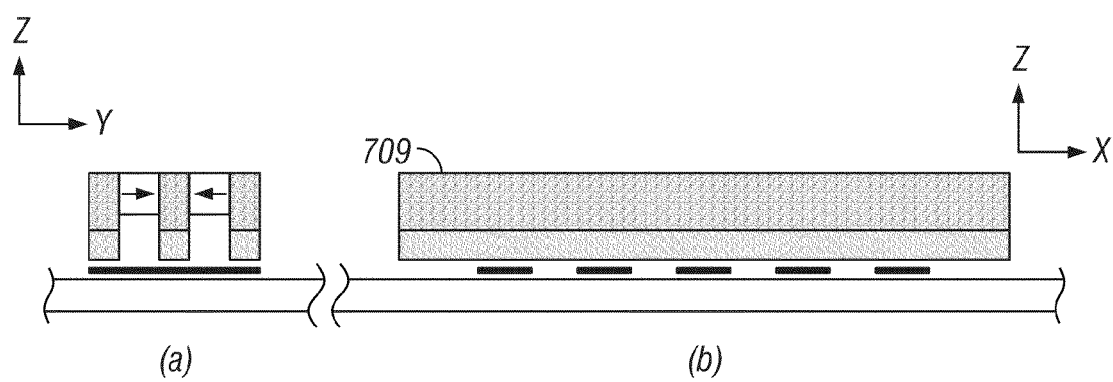
FIG. 7 shows the layout of a another embodiment of a shear wave transducer.
Figure 8A:
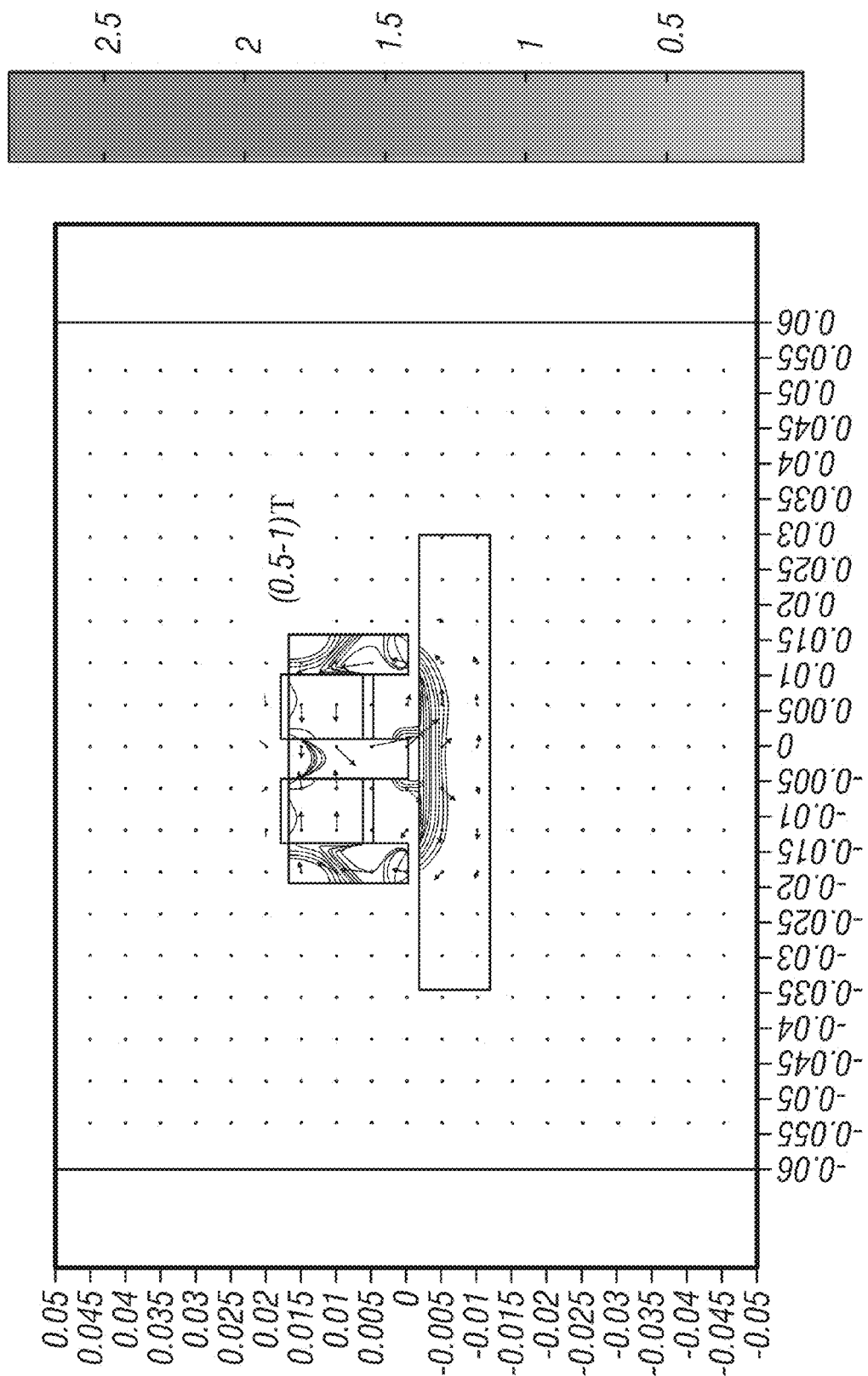
FIGS. 8(a) and 8(b) show results of 2-D simulation of the transducer of FIG. 7 showing the isolines of the static magnetic field and the RF magnetic field, FIG. 9 (prior art) shows a layout of a prior art transducer for Lamb wave generation.
Figure 8B:
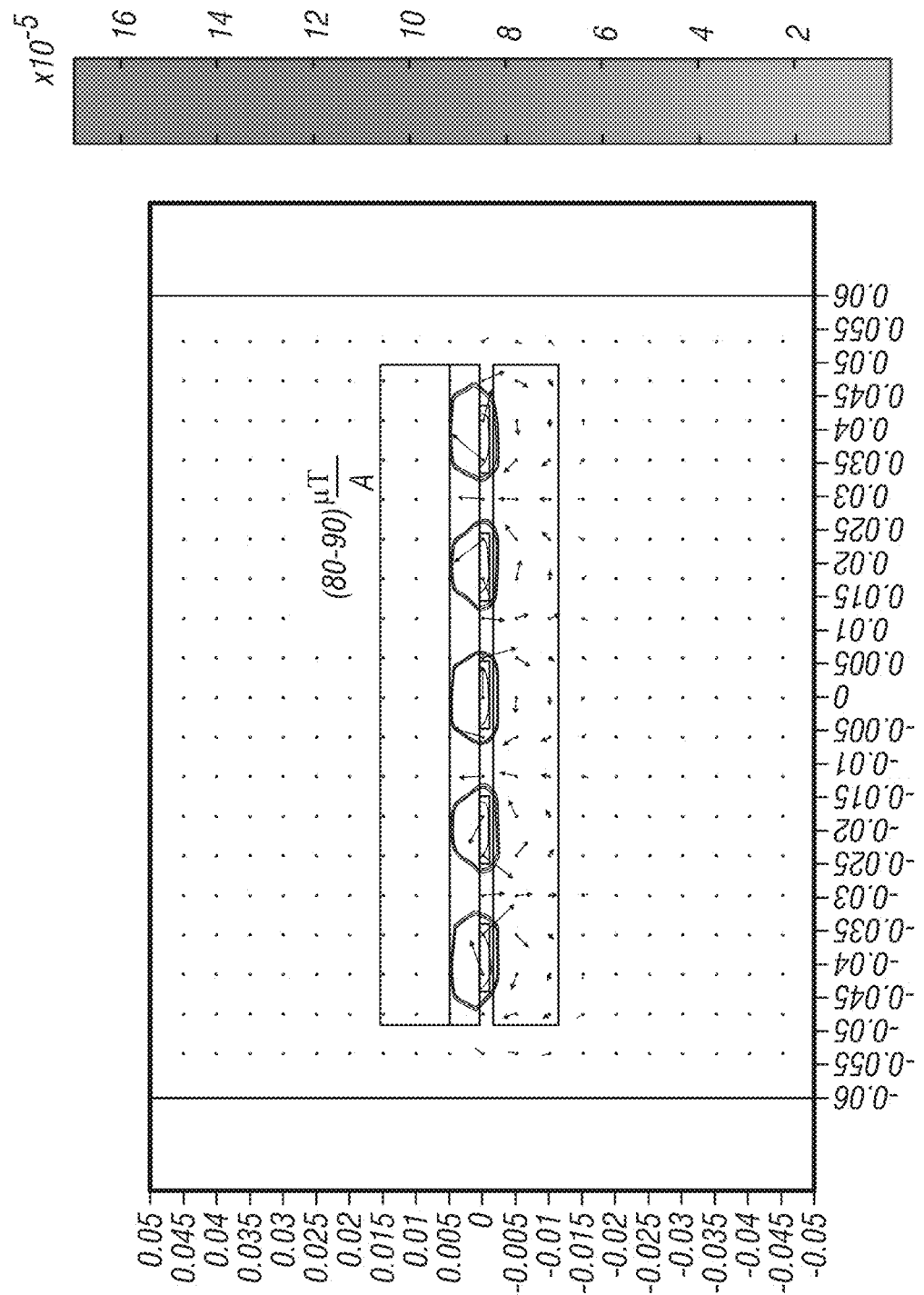

FIG. 7 represents another embodiment of the shear wave EMAT. In addition to the magnetic shoes, a conductive high saturation magnetic member 709 is added. The configurations of the magnetic fields (See FIGS. 8a-8b) as well as the effect of the non-conductive soft magnetic material are basically the same as in the EMAT of the FIG. 5.

Figure 9:
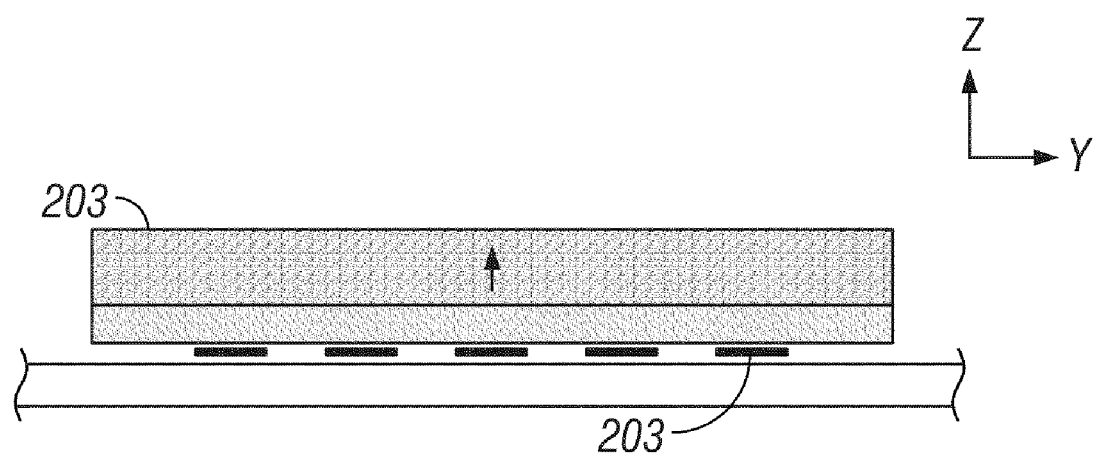
Figure 10B:
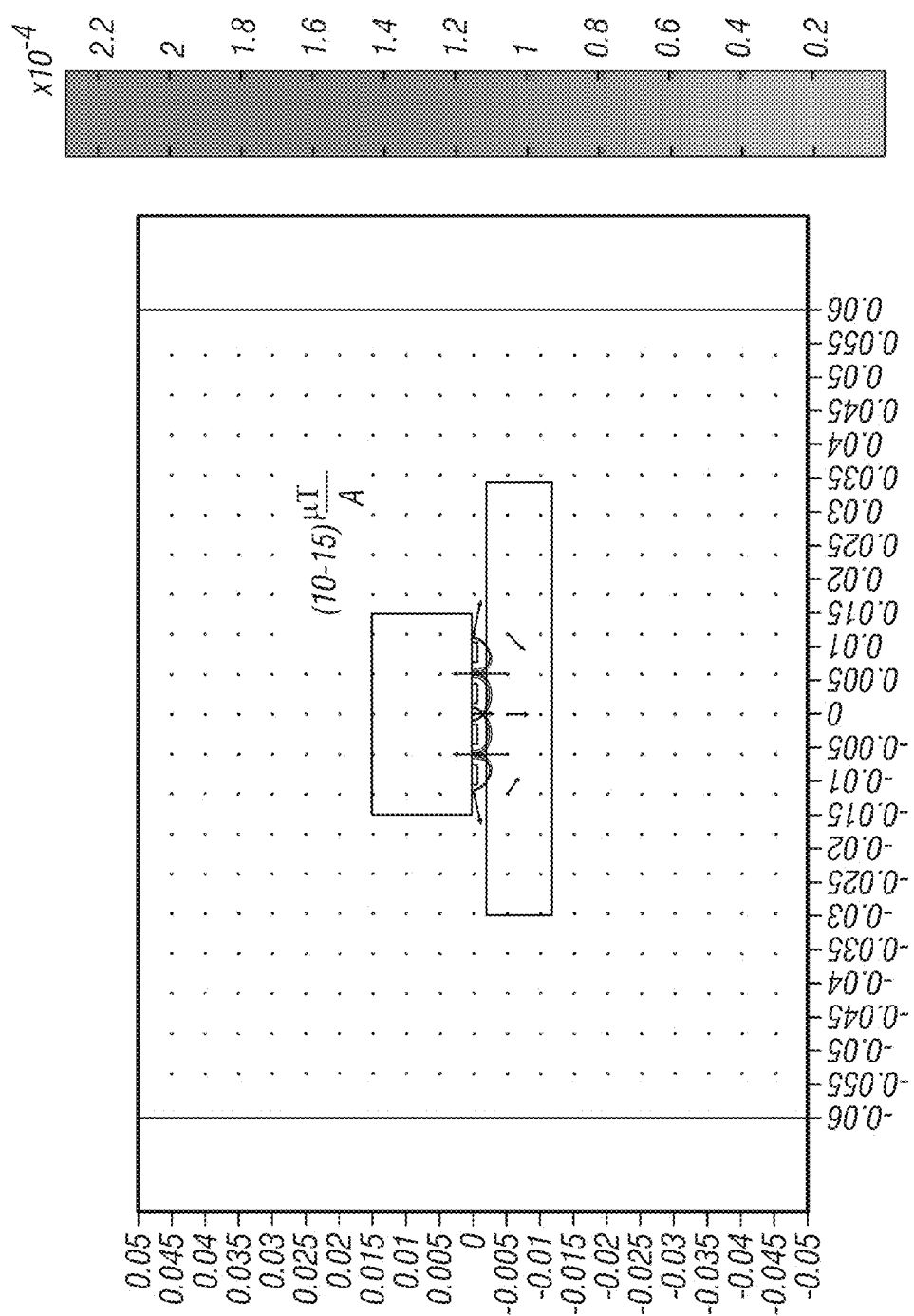
Figure 10C:
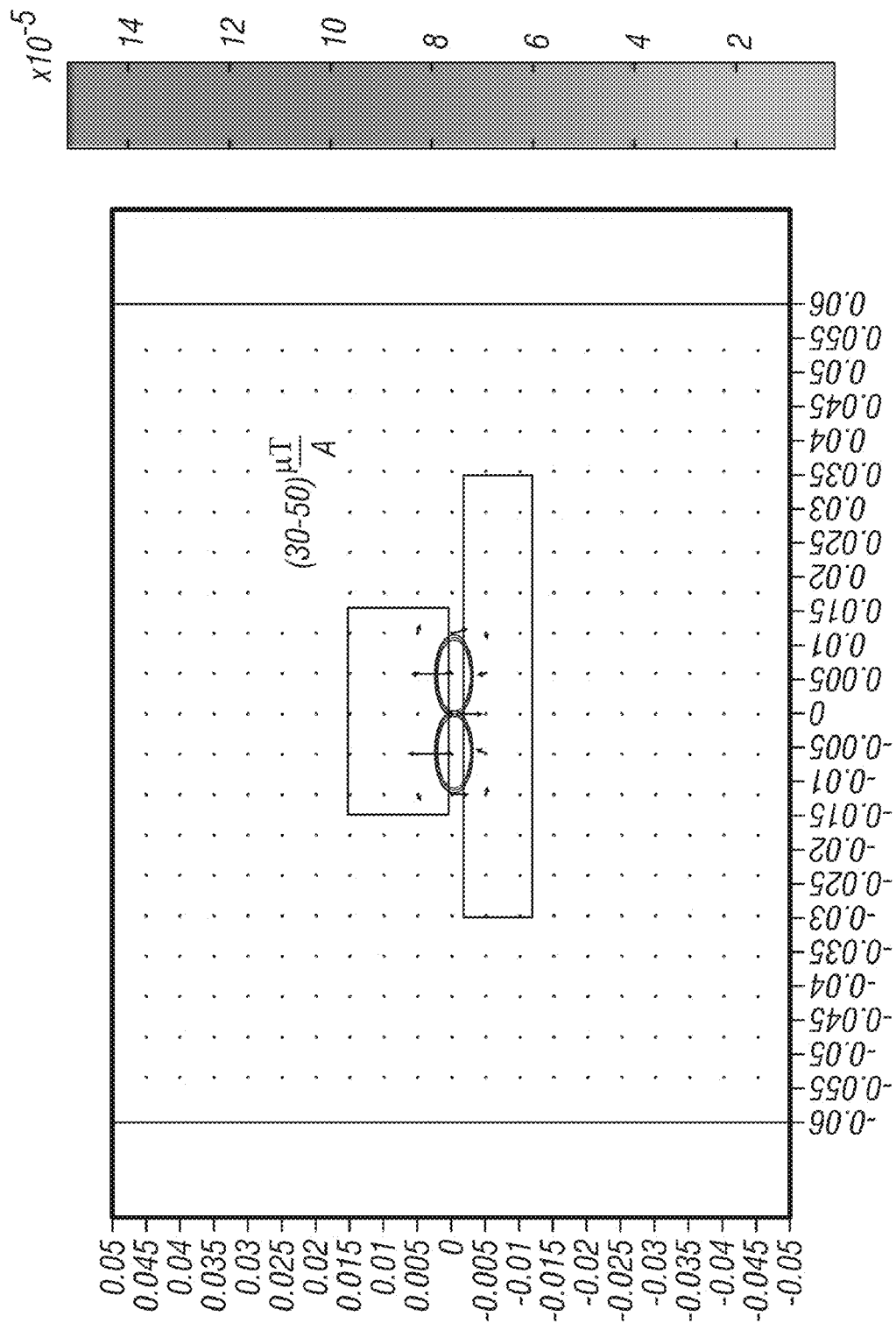

FIG. 9 shows a Lamb wave EMAT of prior art. Presented in the FIGS. 10a, 10b and 10c are the static magnetic field, the RF magnetic field, and the RF magnetic field with a hypothetical nonconductive magnet.

Figure 11:
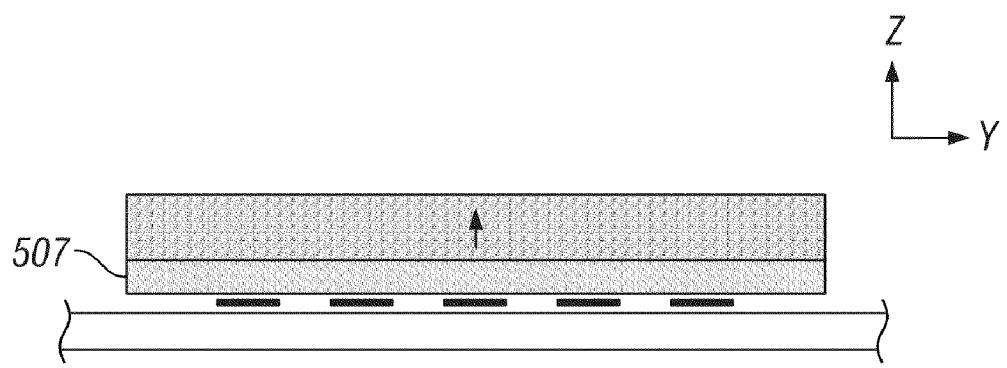
FIG. 11 shows the layout of a modified Lamb wave transducer.
Figure 12A:
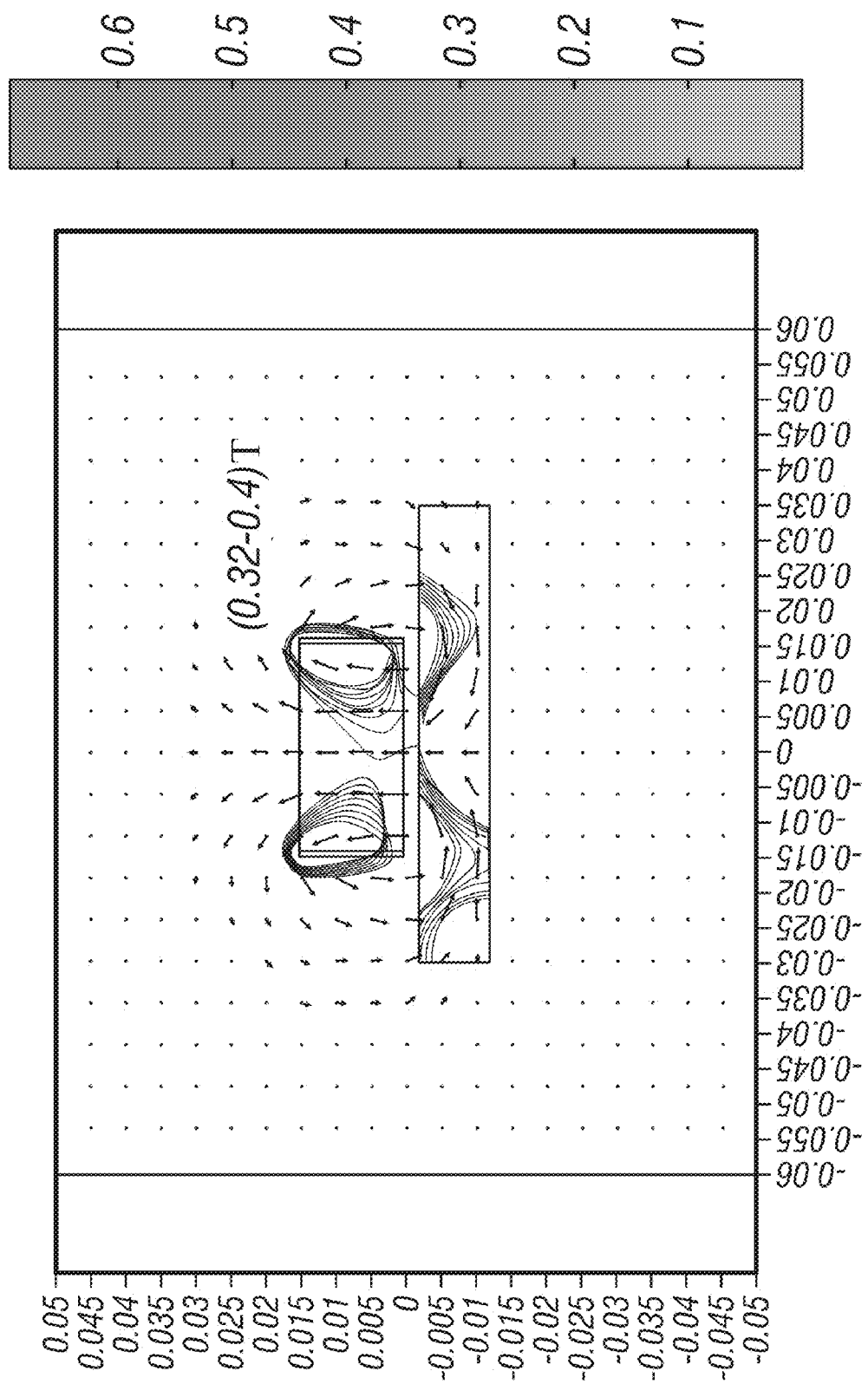
FIGS. 12(a) and 12(b) show results of 2-D simulation of the transducer of FIG. 11 showing the isolines of the static magnetic field and the RF magnetic field.
Figure 12B:
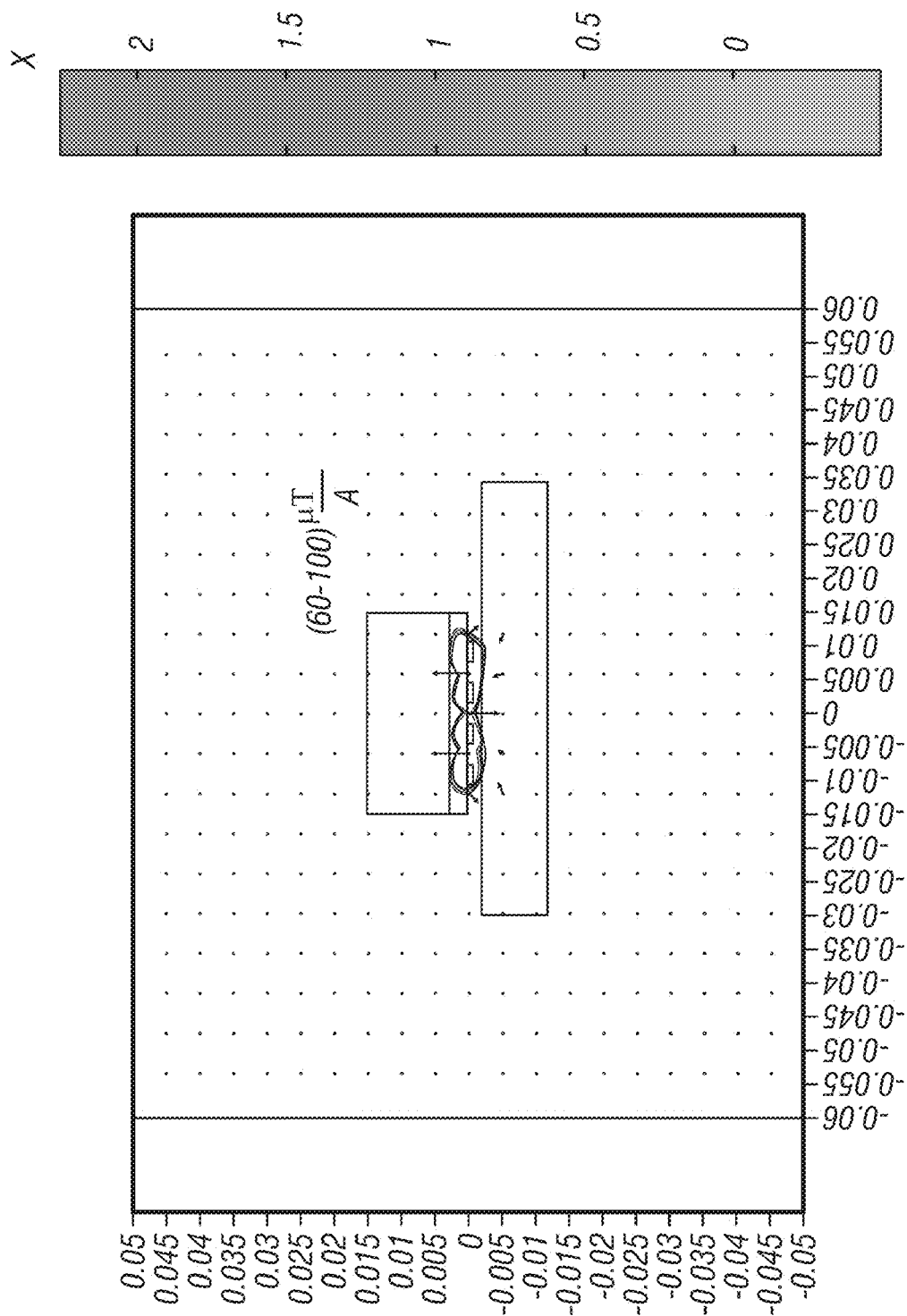

A design using a magnetic shield layer made of the above specified non-conductive soft magnetic material is presented in the FIG. 11. The presence of the layer 507 significantly increases the RF efficiency. Compare FIG. 12b with FIG. 10b.

Figure 13:
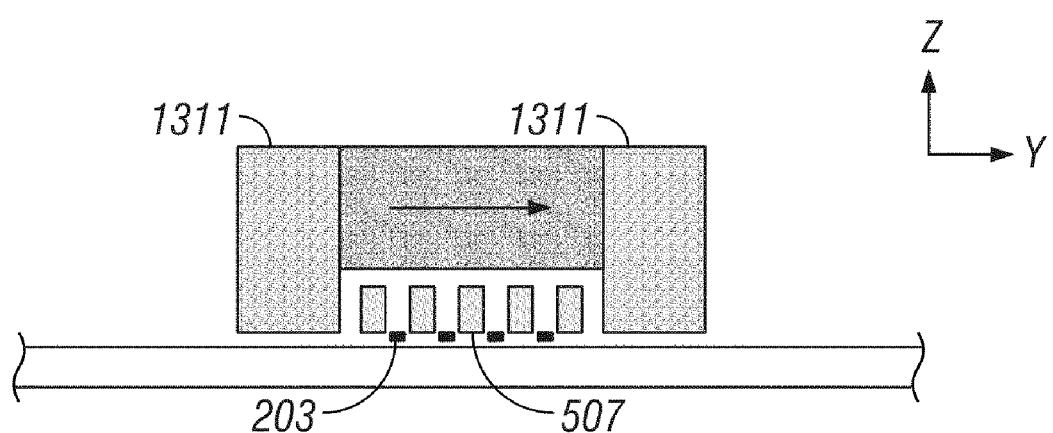
FIG. 13 shows the layout of another embodiment of a Lamb wave transducer.
Figure 14A:
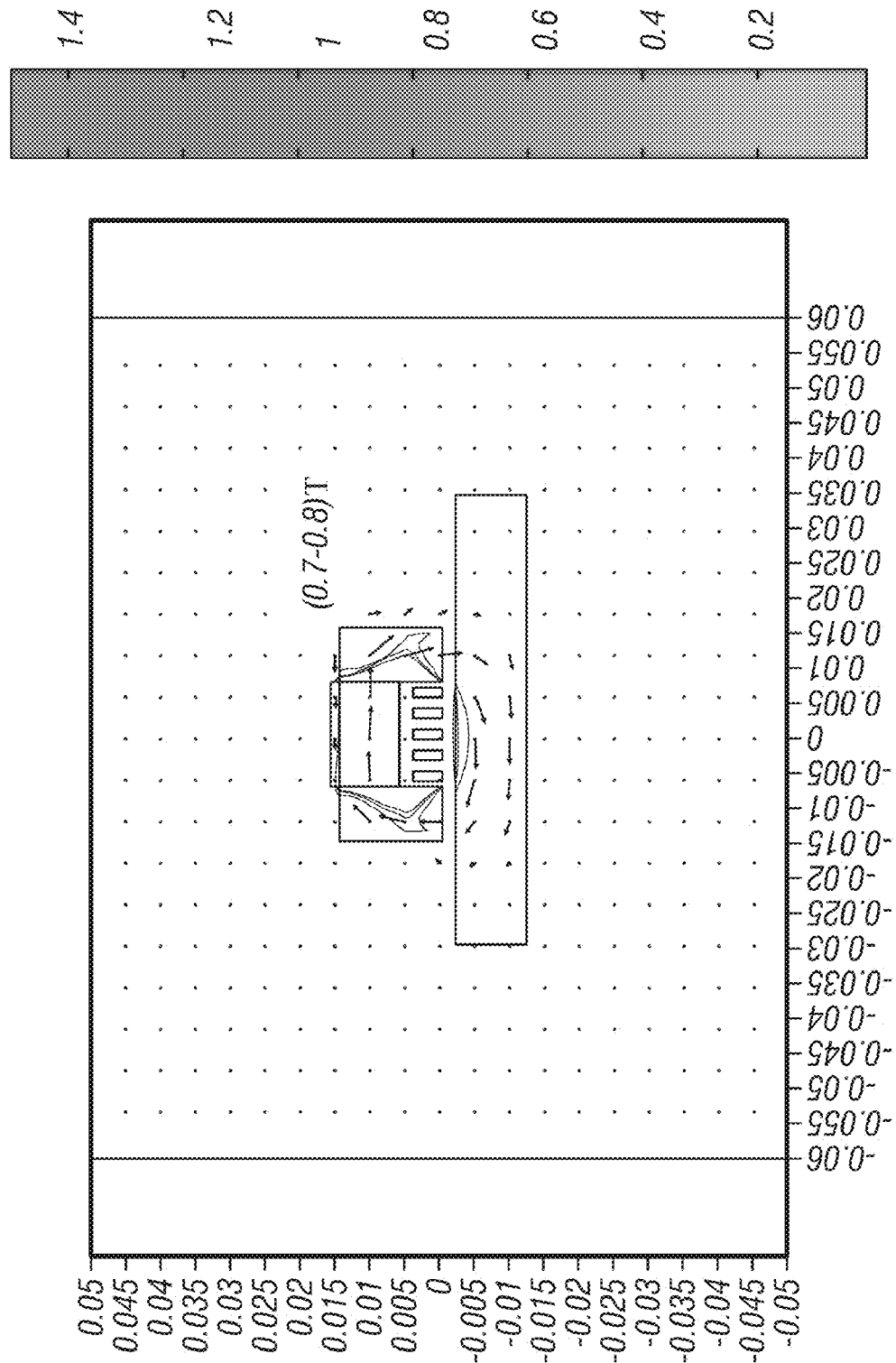
FIGS. 14(a) and 14(b) show results of 2-D simulation of the transducer of FIG. 12 showing the isolines of the static magnetic field and the RF magnetic field.
Figure 14B:
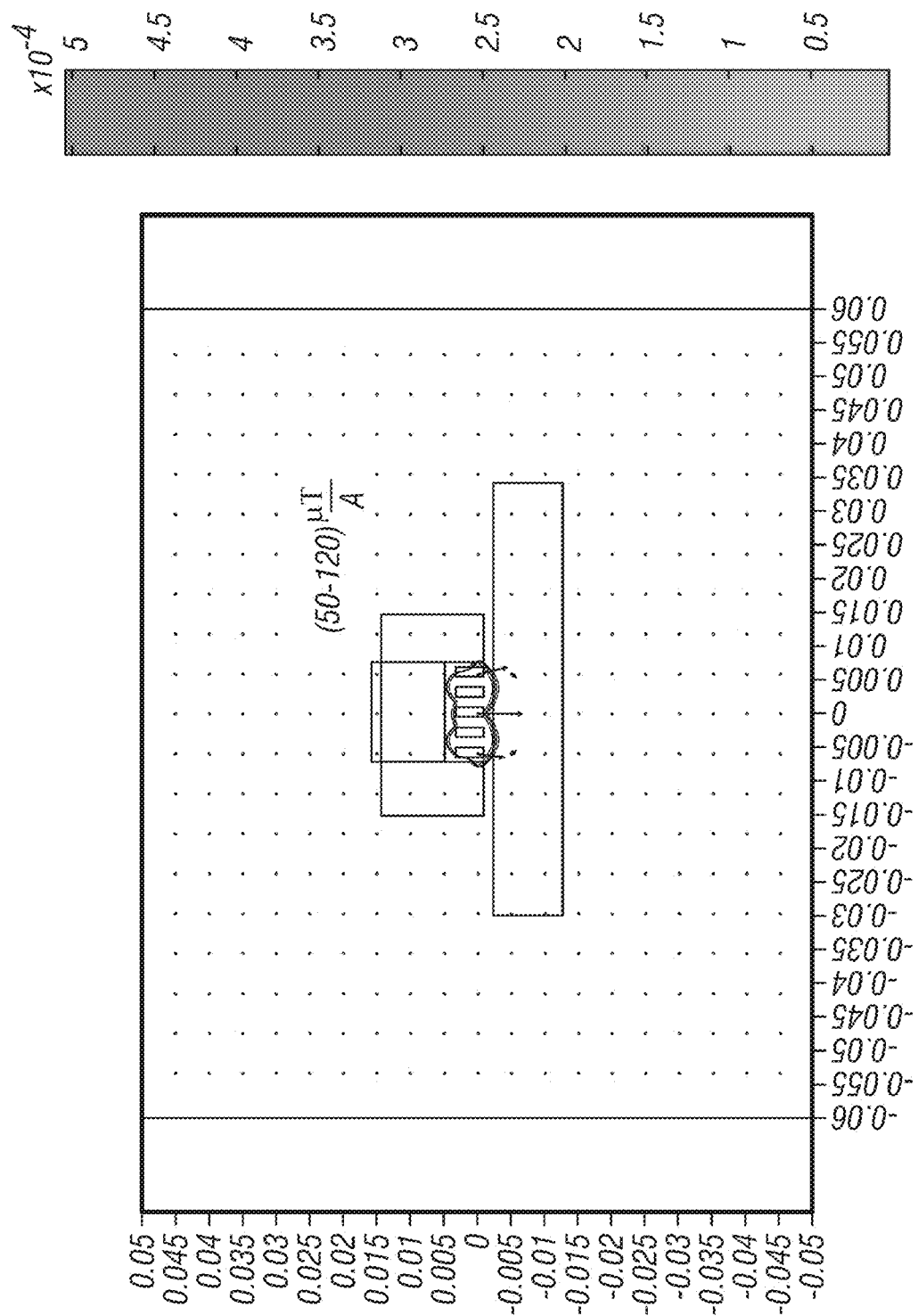

Another configuration for a Lamb wave EMAT using the specified above nonconductive soft magnetic material is presented in FIG. 13. The transducer includes a yoke 1311 made of soft magnetic material. The transducer demonstrates better efficiency for both static magnetic field and RF magnetic field. Compare FIG. 14(a) with FIG. 10(a) and FIG. 14(b) with FIG. 10(b).

Figure 15A:
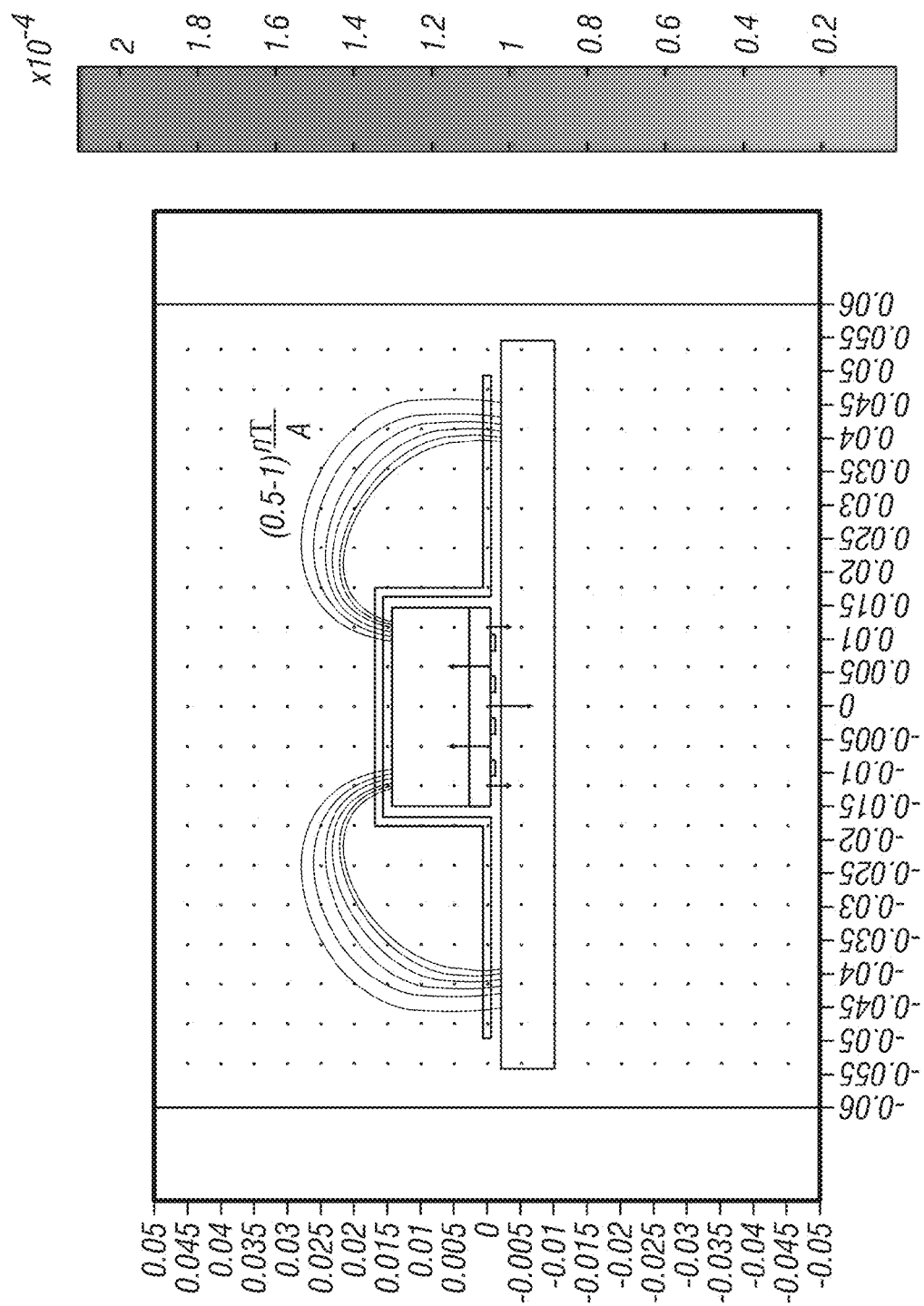
FIGS. 15(a), 15(b) and 15(c) show the effect of an EM (conductive shield) on the stray RF field that may result in cross-talk between the transmit/receive wires: for no shielding, partial shielding and complete shielding respectively.
Figure 15B:
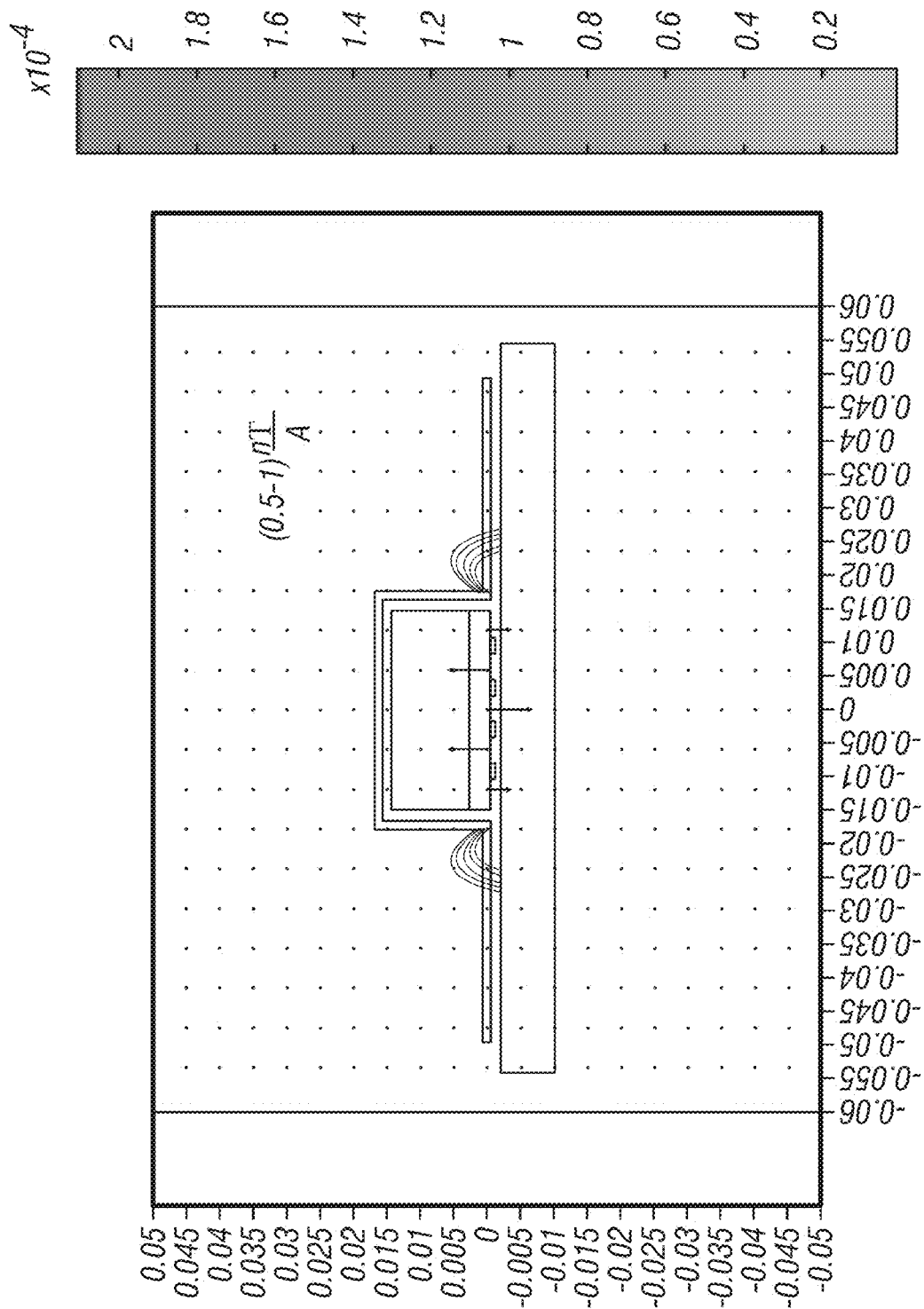
Figure 15C:
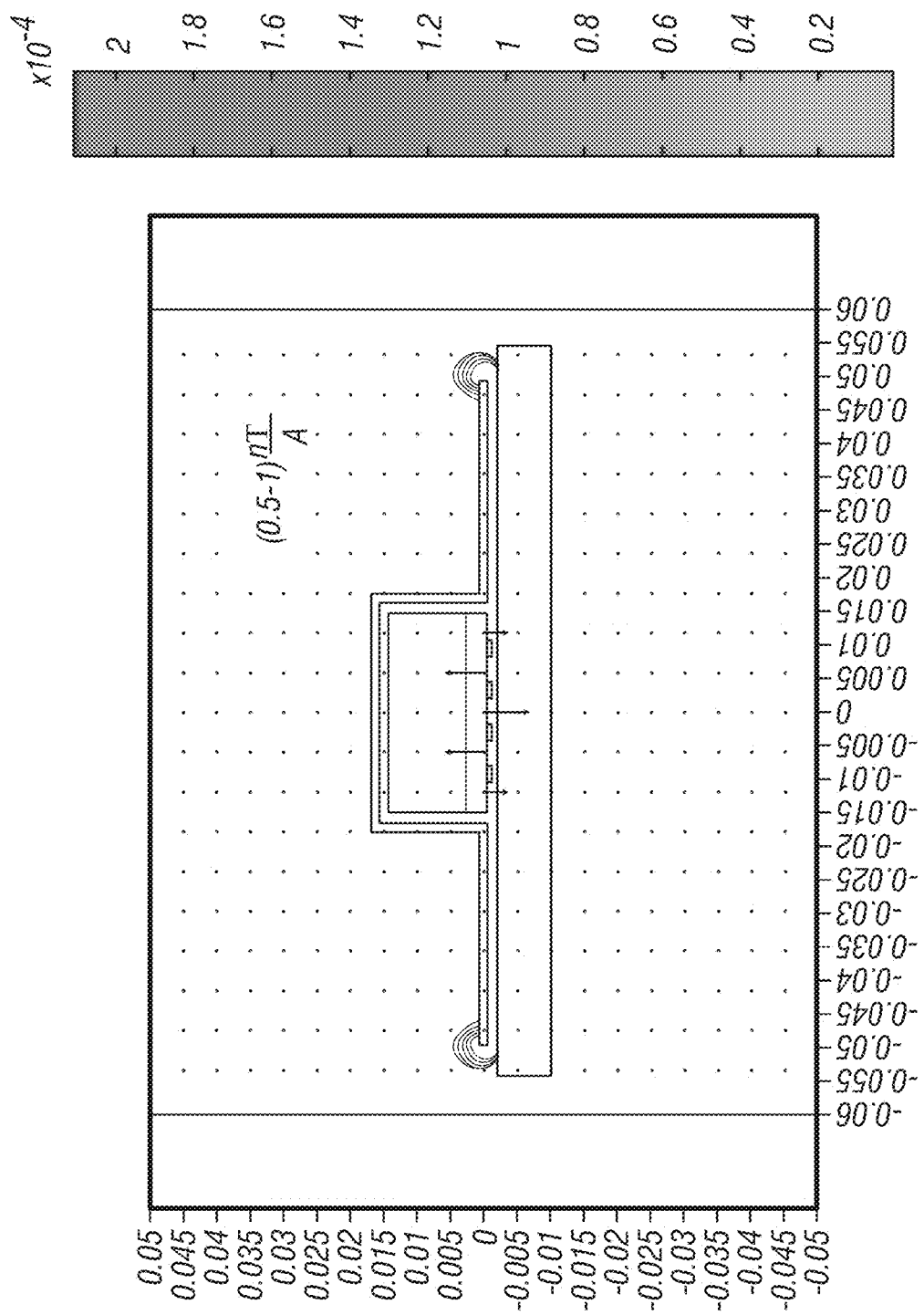

FIGS. 15(a), 15(b), 15(c) show the effect of a EM (conductive) shield on the stray RF magnetic field that may be a source of cross-talk (direct coupling) between two EMATs: one used in transmit mode and another used in receive mode. The cross-talk is most severe when the acoustic waves propagation parameters are measured with two closely placed EMATs (e.g. inside a tubular). The figures show positions of a few RF magnetic field iso-lines in three cases. In FIG. 15(a), there is no shield (in the model the conductivity of the shield is set to 0). In FIG. 15(b), only the central part of the shield is active (the conductivity of the side wings is set to 0). In FIG. 15(c), the effect of full shielding is shown. For simplicity the non-zero conductivity was set to infinity. The effect of the shield is obvious: the same RF field is left much closer to the transducer compared to the "no shield" situation.

The disclosure above has been limited to specific types of waves produced in the tubular. This is not to be construed as a limitation, and the novel features of the present disclosure may be used with other prior art devices to generate a compressional wave, a shear wave, a transversely polarized shear wave, a Lamb wave, and/or a Rayleigh wave.

In a practical device, the signals received by the receive wire that are indicative of the motion of the object being examined are processed by a processor that may be downhole or uphole. Fundamental to the processing is the determination of a velocity of propagation. This may be done by making measurements of a propagating wave using a second transducer displaced from the first transducer, or by making measurements with different portions of the transducer discussed above. The transmitting and receiving transducers may be circumferentially disposed on the outside of a logging tool and/or axially disposed on the outside of the logging tool. Thus, it is possible to determine the velocity of propagation of various types of waves in axial and/or circumferential directions.

Implicit in the control and processing of the data is the use of a computer program on a suitable machine readable medium that enables the processor to perform the control and processing. The machine readable medium may include ROMs, EPROMs, EEPROMs, Flash Memories and Optical disks. Such a computer program may output the results of the processing to a suitable tangible medium. This may include a display device and/or a memory device.

What is claimed is:

1. An apparatus configured to evaluate a tubular, the apparatus comprising:
    an electromagnetic coupling device comprising a coil, a magnet; and
    a non-conductive shield comprising a soft magnetic material, configured to be conveyed into the tubular and coupling acoustic energy within the tubular; wherein the non-conductive shield is configured to shield the magnet from a radio frequency (RF) field of the coil and boost a magnetic field at a surface of the tubular.

2. The apparatus of claim 1, wherein the coupling device is further configured to propagate an acoustic wave in the tubular.

3. The apparatus of claim 1, wherein the coupling device is further configured to record an acoustic wave propagating in the tubular.

4. The apparatus of claim 1 wherein the electromagnetic coupling device is further configured to form a wave within the tubular, the wave having a polarization that is that of at least one of (i) compressional wave, (ii) a shear wave, (iii) a transversely polarized shear wave, (iv) a Lamb wave, or (v) a Rayleigh wave.

5. The apparatus of claim 1 wherein the tubular comprises a casing in a wellbore, the apparatus further comprising a logging tool including the electromagnetic coupling device.

6. The apparatus of claim 5 further comprising a plurality of electromagnetic coupling devices disposed on the logging tool.

7. The apparatus of claim 6 wherein the plurality of electromagnetic coupling devices are positioned: (i) axially spaced apart, or (ii) circumferentially spaced apart.

8. The apparatus of claim 6 further comprising a processor configured to determine a velocity of propagation of an acoustic wave in the tubular using a signal generated by one of the plurality of electromagnetic coupling devices and received by another of the plurality of electromagnetic coupling devices.

9. The apparatus of claim 1 wherein the non-conductive shield further comprises a material having a high saturation flux density.

10. A method of evaluating a tubular, the method comprising:
    conveying an electromagnetic (EMAT) coupling device comprising a coil, a magnet and a non-conductive shield comprising a soft magnetic material into the tubular;
    conveying an electrical current to the coil;
    using the non-conductive shield to shield the magnet from a radio frequency (RF) field of the coil and boost a magnetic field at a surface of the tubular, and
    coupling acoustic energy into the tubular.

11. The method of claim 10 wherein coupling the acoustic energy further comprises propagating an acoustic wave in the tubular.

12. The method of claim 10 wherein coupling the acoustic energy further comprises recording an acoustic wave propagating in the tubular.

13. The method of claim 10 further comprising using the electromagnetic coupling device to form a wave within the tubular, the wave having a polarization that is that of at least one of (i) a compressional wave, (ii) a shear wave, (iii) a transversely polarized shear wave, (iv) a Lamb wave, or (v) a Rayleigh wave.

14. The method of claim 10 wherein the tubular comprises a casing in a wellbore, the method further comprising disposing the electromagnetic coupling device on a logging tool.

15. The method of claim 14 further comprising using a plurality of electromagnetic coupling devices disposed on the logging tool.

16. The method of claim 15 further comprising positioning the plurality of electro-magnetic coupling devices on the logging tool in: (i) an axially spaced apart arrangement, or (ii) a circumferentially spaced apart arrangement.

17. The method of claim 15 further comprising determining a velocity of propagation of an acoustic wave in the tubular using a signal generated by one of the plurality of electromagnetic coupling devices and received by another of the plurality of electromagnetic coupling devices.

18. A non-transitory computer-readable medium product having stored thereon instructions that when read by a processor cause the processor to perform a method, the method comprising:
    using an electromagnetic coupling device including a coil, a magnet and a non-conductive shield including a soft magnetic material in a tubular and producing a wave in the tubular having a polarization that is at least one of: (i) a compressional wave, (ii)-a shear wave, (iii) a transversely polarized shear wave, (iv) a Lamb wave, or (v) a Rayleigh wave
    wherein the non-conductive shield is configured to shield the magnet from a radio frequency (RF) field of the coil and boost a magnetic field at a surface of the tubular.

19. The medium of claim 18 further comprising at least one of:
    (i) a ROM, (ii) an EPROM, (iii) an EEPROM, (iv) a flash memory, or (v) an optical disk.

* * * * *